(12) United States Patent
Stefanov et al.

(10) Patent No.: US 11,554,213 B2
(45) Date of Patent: Jan. 17, 2023

(54) INJECTOR NEEDLE INSERTION RETRACTION ASSEMBLY

(71) Applicant: SHL MEDICAL AG, Zug (CH)

(72) Inventors: Slobodan Stefanov, Deerfield Beach, FL (US); Johnathan Weiss, Pompano Beach, FL (US)

(73) Assignee: SHL MEDICAL AG, Zug (CH)

( * ) Notice: Subject to any disclaimer, the term of this patent is extended or adjusted under 35 U.S.C. 154(b) by 0 days.

(21) Appl. No.: 15/734,291

(22) PCT Filed: Sep. 12, 2019

(86) PCT No.: PCT/EP2019/074302
§ 371 (c)(1),
(2) Date: Dec. 2, 2020

(87) PCT Pub. No.: WO2020/058069
PCT Pub. Date: Mar. 26, 2020

(65) Prior Publication Data
US 2021/0220555 A1    Jul. 22, 2021

Related U.S. Application Data

(60) Provisional application No. 62/735,045, filed on Sep. 22, 2018.

(30) Foreign Application Priority Data

Nov. 8, 2018 (EP) .................................... 18205273

(51) Int. Cl.
*A61M 5/158*    (2006.01)
(52) U.S. Cl.
CPC ..... *A61M 5/158* (2013.01); *A61M 2005/1585* (2013.01)

(58) Field of Classification Search
CPC .. A61M 5/142; A61M 5/158; A61M 5/14244; A61M 5/14248;
(Continued)

(56) References Cited

U.S. PATENT DOCUMENTS 9,119,913 B2 * 9/2015 Lanigan ........... A61B 5/150175
10,456,521 B2 * 10/2019 Stefanov ............. A61M 5/1452
(Continued)

FOREIGN PATENT DOCUMENTS

CN        1863566 A  * 11/2006   ........ A61M 5/14248
CN      206518747 U      9/2017
(Continued)

OTHER PUBLICATIONS

International Search Report and Written Opinion for Int. App. No. PCT/EP2019/074302, dated Nov. 26, 2019.
(Continued)

*Primary Examiner* — Jason E Flick
*Assistant Examiner* — Adam J. Cermak
(74) *Attorney, Agent, or Firm* — McDonnell Boehnen Hulbert & Berghoff LLP

(57) ABSTRACT

A needle insertor for a medicament delivery device is presented having a driver having a first part movably arranged within the case and a second part connected to the base, a needle assembly movably held by the first part in the case, a rotator arranged in the case and configured to engage the first part for moving the driver, an energy accumulation member configured to interact with the rotator for applying a rotational force on the rotator, a movable stop arranged on the base and configured to interact with the rotator for preventing the rotator from rotating. The first part has a first position where the needle assembly is held inside the case, a second position where the needle portion is positioned outside the case after being moved to pass through the
(Continued)

injection site end, and a third position where the needle portion is positioned inside the case.

19 Claims, 15 Drawing Sheets

(58) Field of Classification Search
CPC ........... A61M 2005/1585; A61M 2005/14268; A61M 2005/14252; A61M 2005/14256; A61M 2005/1426
See application file for complete search history.

(56) References Cited

U.S. PATENT DOCUMENTS

| | | | |
|---|---|---|---|
| 10,549,030 B2 * | 2/2020 | Kim | A61M 5/145 |
| 11,129,936 B2 * | 9/2021 | Gibson | A61M 5/1454 |
| 11,185,629 B2 * | 11/2021 | Weibel | A61J 1/20 |
| 2008/0051714 A1 * | 2/2008 | Moberg | A61M 5/1413 604/135 |
| 2008/0051718 A1 * | 2/2008 | Kavazov | A61M 5/1413 604/93.01 |
| 2008/0051738 A1 * | 2/2008 | Griffin | A61M 5/158 604/272 |
| 2008/0269687 A1 * | 10/2008 | Chong | A61M 5/1413 604/180 |
| 2010/0286714 A1 * | 11/2010 | Gym | A61M 5/158 606/139 |
| 2014/0058353 A1 * | 2/2014 | Politis | A61M 5/158 604/164.04 |
| 2015/0265768 A1 * | 9/2015 | Vazquez | A61M 5/162 604/67 |
| 2015/0306307 A1 * | 10/2015 | Cole | A61M 5/158 604/508 |
| 2016/0184512 A1 * | 6/2016 | Marbet | A61M 5/14248 604/157 |
| 2016/0199590 A1 * | 7/2016 | Schabbach | A61M 5/3287 604/240 |
| 2016/0213837 A1 * | 7/2016 | Schabbach | A61M 5/14244 |
| 2016/0213838 A1 * | 7/2016 | Schabbach | A61M 5/3287 |
| 2018/0021508 A1 * | 1/2018 | Destefano | A61M 5/14244 604/151 |
| 2018/0193557 A1 * | 7/2018 | Johnson | A61M 5/14526 |
| 2019/0009019 A1 * | 1/2019 | Shor | A61M 5/14216 |
| 2019/0022305 A1 * | 1/2019 | Møller | A61M 5/14248 |
| 2019/0030240 A1 * | 1/2019 | Cabiri | A61M 5/14248 |
| 2019/0365987 A1 * | 12/2019 | Gibson | A61M 5/14248 |
| 2020/0023122 A1 * | 1/2020 | McCullough | A61M 5/14248 |
| 2020/0061286 A1 * | 2/2020 | Giambattista | A61M 5/158 |
| 2020/0230313 A1 * | 7/2020 | Mojarrad | A61M 5/142 |
| 2020/0316297 A1 * | 10/2020 | Kapas | A61M 5/14244 |
| 2021/0046252 A1 * | 2/2021 | Koch | A61M 5/1424 |
| 2021/0128823 A1 * | 5/2021 | Shaked | A61M 5/158 |
| 2021/0402083 A1 * | 12/2021 | Gibson | A61M 5/158 |
| 2021/0402084 A1 * | 12/2021 | Coker | A61M 25/0606 |
| 2022/0002009 A1 * | 1/2022 | Grant | A61M 5/14248 |

FOREIGN PATENT DOCUMENTS

| | | | |
|---|---|---|---|
| CN | 206822918 U | 1/2018 | |
| CN | 107823760 A | 3/2018 | |
| CN | 107847664 A | 3/2018 | |
| CN | 107921200 A | 4/2018 | |
| EP | 3260146 A1 * | 12/2017 | ......... A61M 5/1413 |
| EP | 3260151 A1 * | 12/2017 | ........ A61M 5/14212 |
| EP | 3501576 A1 * | 6/2019 | ........ A61M 5/14248 |
| EP | 3539592 A1 * | 9/2019 | ............ A61M 39/14 |
| EP | 3574941 A1 * | 12/2019 | ........ A61M 5/14212 |
| EP | 3603700 A1 * | 2/2020 | ........ A61M 5/14248 |
| EP | 3003426 B1 * | 3/2021 | ........ A61M 5/14216 |
| JP | 2018505031 A * | 2/2018 | ........ A61M 5/14248 |
| SE | 521913 C2 * | 12/2003 | ........ A61M 15/0036 |
| WO | 2009/010399 A1 | 1/2009 | |
| WO | WO-2013153041 A2 * | 10/2013 | ........ A61M 5/14248 |
| WO | 2015/164645 A1 | 10/2015 | |
| WO | WO-2016074850 A1 * | 5/2016 | ........ A61M 5/14248 |
| WO | 2016/130679 A2 | 8/2016 | |
| WO | WO-2016130679 A2 * | 8/2016 | ........ A61M 5/14244 |
| WO | WO-2018024625 A1 * | 2/2018 | ........ A61M 5/14248 |
| WO | WO-2018096149 A1 * | 5/2018 | .......... A61M 5/1409 |
| WO | WO-2018152073 A1 * | 8/2018 | ........ A61M 5/14248 |
| WO | 2018/165499 A1 | 9/2018 | |
| WO | WO-2019014014 A1 * | 1/2019 | ............ A61M 5/142 |
| WO | WO-2019058177 A1 * | 3/2019 | ........ A61M 5/14248 |
| WO | WO-2020143987 A1 * | 7/2020 | ........ A61M 5/14248 |
| WO | WO-2021043577 A1 * | 3/2021 | |

OTHER PUBLICATIONS

CN Office Action for corresponding CN Application No. 201980039515.3, dated Mar. 8, 2022.

* cited by examiner

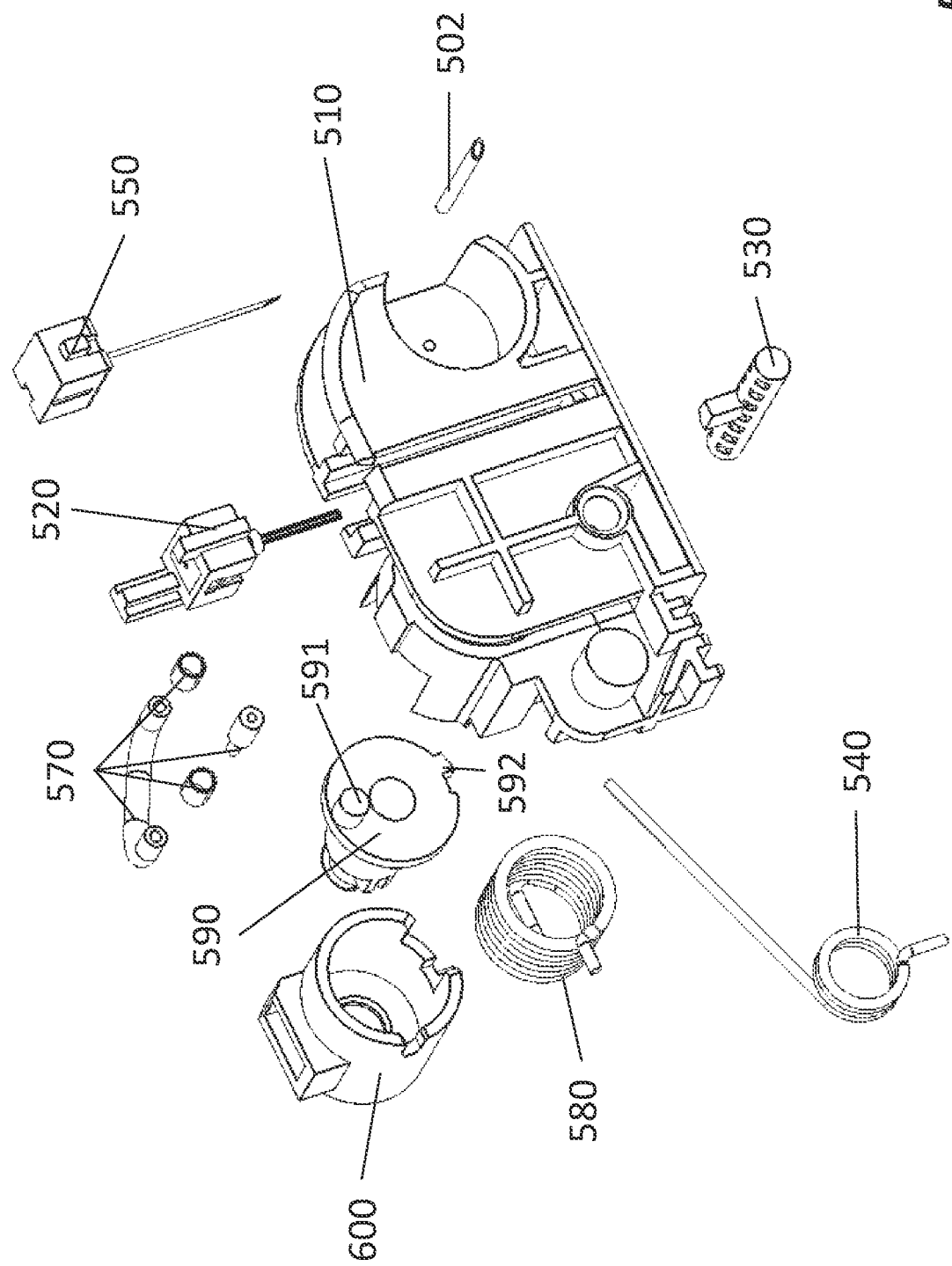

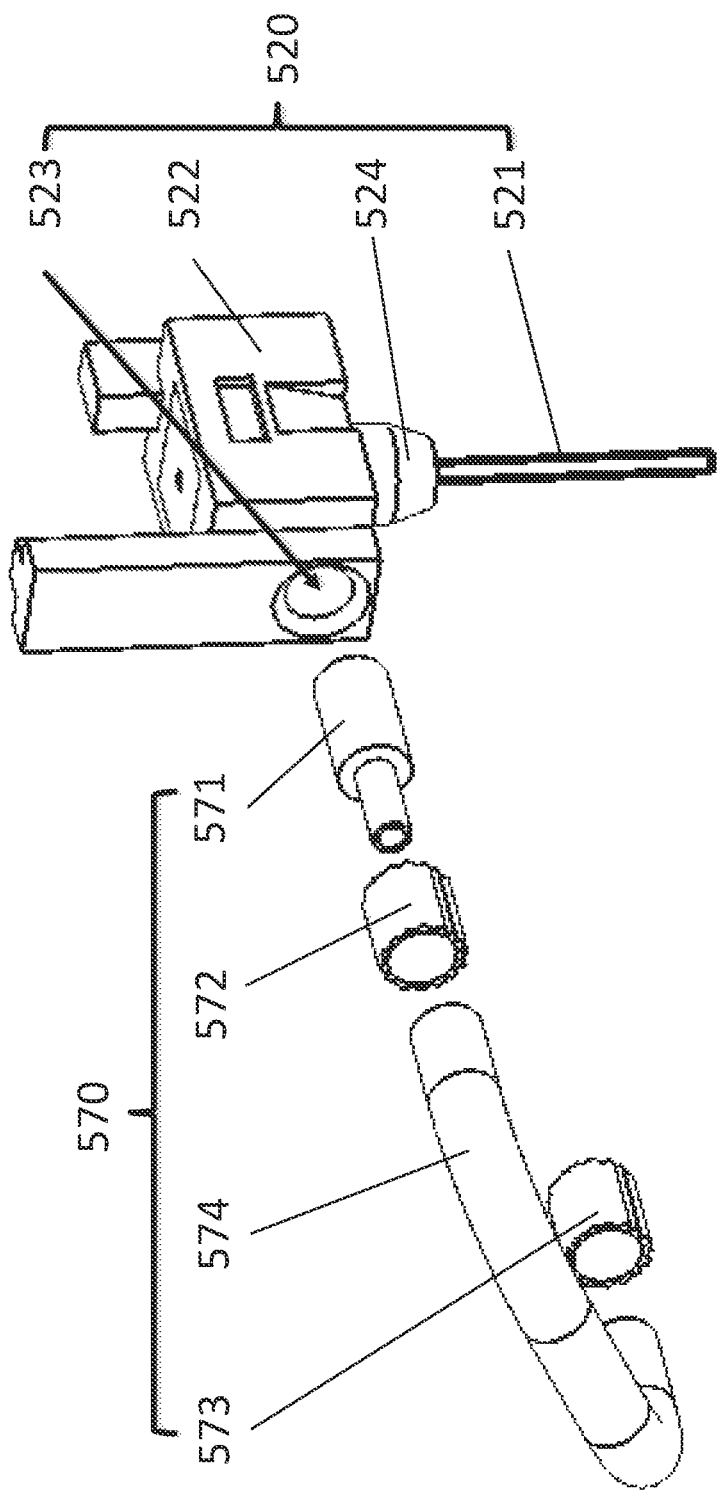

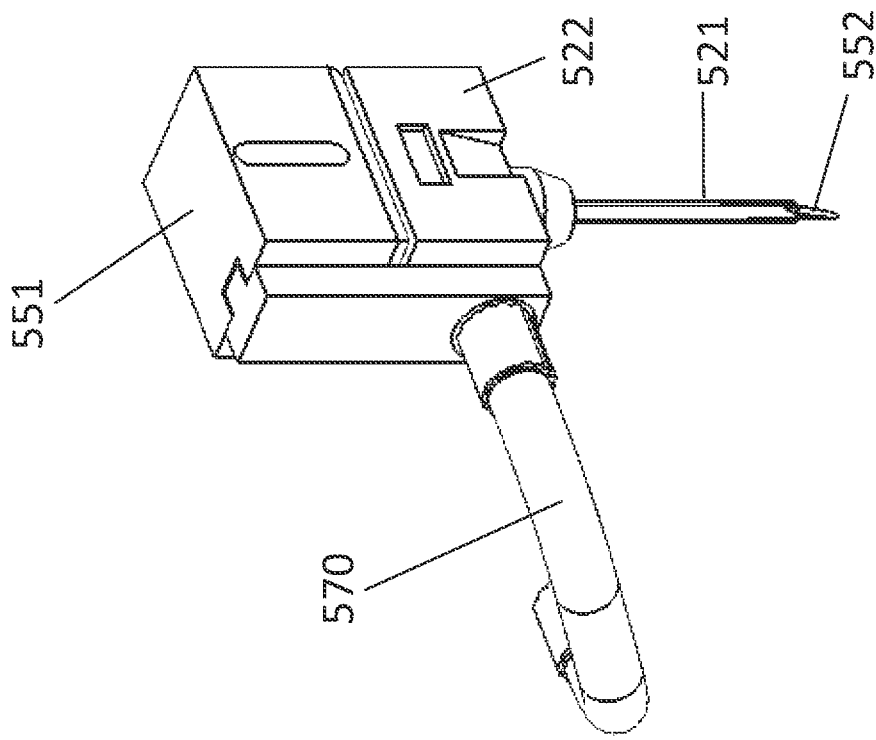
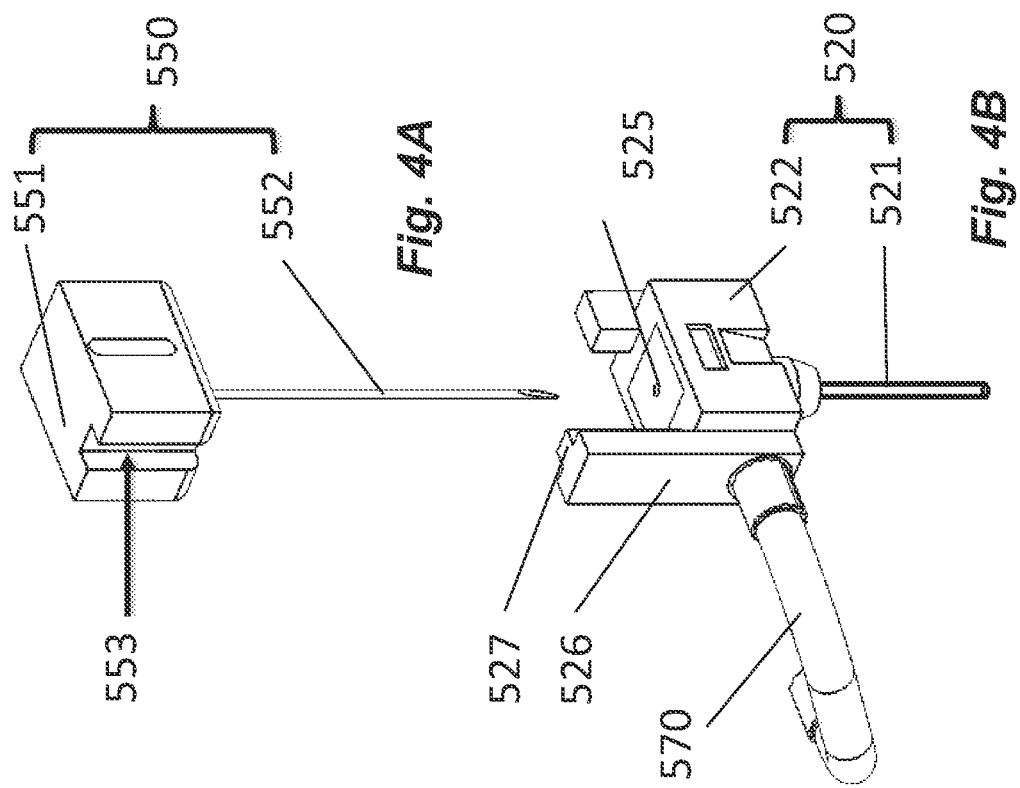

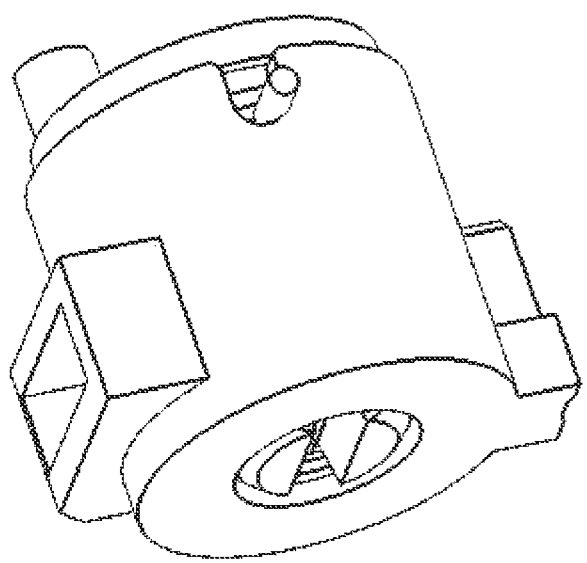
*Fig. 5*
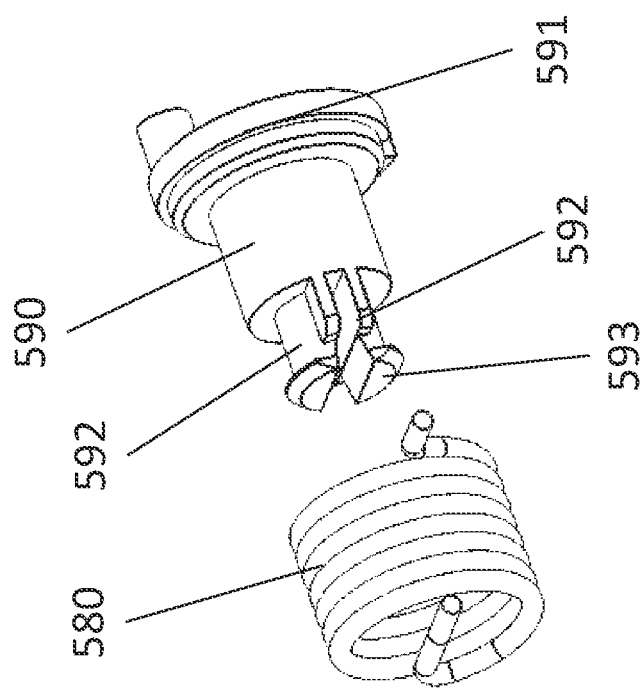
*Fig. 5A*
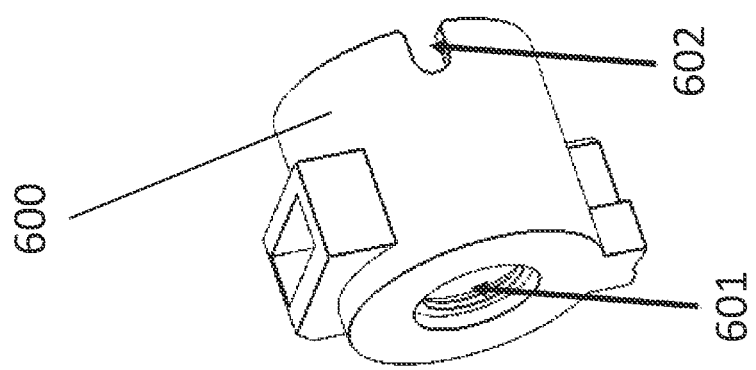

INJECTOR NEEDLE INSERTION RETRACTION ASSEMBLY

CROSS REFERENCE TO RELATED APPLICATIONS

The present application is a U.S. National Phase application pursuant to 35 U.S.C. § 371 of International Application No. PCT/EP2019/074302 filed Sep. 12, 2019, which claims priority to U.S. Provisional Patent Application No. 62/735,045 filed Sep. 22, 2018, and European Patent Application No. 18205273.8 filed Nov. 8, 2018. The entire disclosure contents of these applications are herewith incorporated by reference into the present application.

TECHNICAL AREA

The present disclosure relates to a needle insertion and retraction assembly of a medicament delivery device and in particular to a needle insertion and retraction assembly in which the needle and catheter are inserted at an insertion site and the needle is subsequently withdrawn from the insertion site

BACKGROUND

A large number of people suffering from diabetes use some form of insulin therapy to maintain close control of their glucose levels. Currently, there are two principal modes of daily, insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. Infusion pumps, although more complex than syringes and pens, offer the advantages of continuous infusion of insulin, precision dosing and programmable delivery schedules. This results in closer blood glucose control and an improved feeling of wellness.

The use of an infusion pump further requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive that retains the base on the skin during use. The hub or base may be applied to the skin manually or with the aid of a manual or automatic insertion device. Often, the insertion device is a separate, stand-alone unit that the user is required to carry and provide.

There are many available versions of infusion sets, including steel cannula infusion sets and soft (flexible) catheter sets. Soft catheter sets are typically inserted into a patient manually with the aid of a steel introducer needle, which is later removed from the patient leaving the soft catheter in place. In another type of infusion set, as noted above, a mechanized insertor is used to automatically insert the introducer needle and catheter, remove the introducer needle, or both. The introducer needle is completely removed from the infusion set before the soft catheter is connected to the insulin pump.

One problem associated with manually inserting and retracting the introducer needle is variability in the insertion and retraction force, speed, smoothness and angle. This variability can lead to an increased rate of catheter insertion failure.

Further, as noted above, the user typically must remove the introducer needle after inserting the cannula. This exposes the user to accidental needle sticks from handling the removed introducer needle.

Accordingly, a need exists for an infusion set that facilitates insertion of the cannula, while reducing the number of components a user must carry and substantially preventing accidental needle sticks.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

These and other aspects of, and advantages with, the present disclosure will become apparent from the following detailed description of the present disclosure and from the accompanying drawings.

According to a main aspect of the disclosure it is characterized by a needle insertor for a medicament delivery device, comprising, a case having a base and an injection site end, a driver having a first part movably arranged within the case and a second part connected to the base, a needle assembly movably held by the first part of the driver in the case, a rotator arranged in the case and configured to interact with the first part of the driver for moving the driver, an energy accumulation member configured to interact with the rotator for applying a rotational force on the rotator, a movable stop arranged on the base and configured to interact with the rotator for preventing the rotator from rotating. The needle assembly includes a needle portion positioned substantially perpendicular to the injection site end.

Further, the first part has a first position where the needle assembly is held inside the case, a second position where the needle portion is positioned outside the case after being moved to pass through the injection site end and pierce an injection site, and a third position where the needle portion is positioned inside the case. In addition, a movable stop is further configured to interact with the rotator for releasing the rotator and allow the rotational force from the energy accumulation member to rotate the rotator to further allow the first part to move between said positions.

In one embodiment, the needle insertor may further comprise a cannula assembly configured to interact with the needle assembly, wherein the cannula assembly remains within the case when the first part is in the first position. The cannula assembly is moved by the needle assembly to enter the injection site when the first part is in the second position.

Further, the cannula assembly includes a cannula base portion and a cannula portion substantially perpendicular to the injection site end. The cannula portion is coupled with the cannula base portion and configured to enter the injection site when the first part is in the second position. The cannula portion is positioned in the injection site when the first part is in the second position.

The cannula base portion includes a medicament input opening, wherein the cannula portion and cannula base portion are hollow so that a medicament can pass through the medicament input opening, the cannula base portion, and exits through the cannula portion.

Further, the needle portion is positioned within the cannula portion when the first part is in the first and second positions, the needle portion is not positioned within the cannula portion when the first part is in the third position.

The cannula base portion is positioned between the needle assembly and the injection site end, wherein the needle assembly interacts with the cannula base portion to move the cannula assembly toward the injection site end when the first part moves from the first position to the second position.

Further, the base includes at least one locking member configured to engage and fix the cannula assembly on the base when the first part reaches the second position.

The base includes a container port for accommodating a medicament container, a piercer coupled with the container port for piercing the medicament container, a medicament path assembly coupled with the base. The medicament tube assembly having a first end connected to the piercer and a second end connected to the cannula assembly, wherein a medicament can flow from the medicament container through the piercer and the medicament tube assembly to enter the cannula assembly.

The needle assembly can further include a needle base portion coupled with the needle portion and configured to be movably held by the first part, wherein the first part of the driver drives the needle base portion to move the needle portion outside the case when moving from the first position to the second position. The first part of driver drives the needle base portion to move the needle portion back inside the case when moving from the second position to the third position.

The rotator further includes an engagement member configured to interact with the first part, wherein the engagement member of the rotator is rotated by the energy accumulation member interacts with the first part to move the first part between said positions.

In one embodiment, the second part of the driver is pivotably fixed on the case. However, in another embodiment, the driver can have a flexible elastic structure, wherein elasticity of the driver allows the second part of the driver to move the first part of the driver to the third position when the engagement member no longer interacts with the first part.

The base includes a first rest configured to accommodate the energy accumulation member and a second rest configured to engage the rotator and keep the rotator rotatably connected to the base. The injection site end of the case includes a first injection site opening configured for the needle assembly to pass through and pierce the injection site. The base includes a second injection site opening corresponding to the first injection site opening, the needle assembly passes through both the first and second injection site openings to pierce the injection site. The base includes a guiding structure forming a channel extending perpendicularly to the injection site end, wherein the needle assembly is at least partially accommodated in the channel while held movably by the first part of the driver.

The needle insertor can further include a sleeve configured to accommodate the rotator and the energy accumulation member, wherein the base includes a sleeve port configured to accommodate the sleeve.

BRIEF DESCRIPTION OF DRAWINGS

In the following detailed description of the present disclosure, reference will be made to the accompanying drawings, of which

FIG. 2 shows an exploded view of the insert assembly according to the first embodiment of the present disclosure.

FIG. 3 shows an exploded view of cannula assembly and medicament path assembly according to the first embodiment of the present disclosure.

FIGS. 4, 4A and 4B show perspective views and exploded views of the needle assembly, cannula assembly, and medicament path assembly as well as a perspective view of said components assembled.

FIGS. 5 and 5A show perspective views and exploded views of the torsion spring, rotator, and sleeve as well as a perspective view of said components assembled.

DETAILED DESCRIPTION

Figure 1:
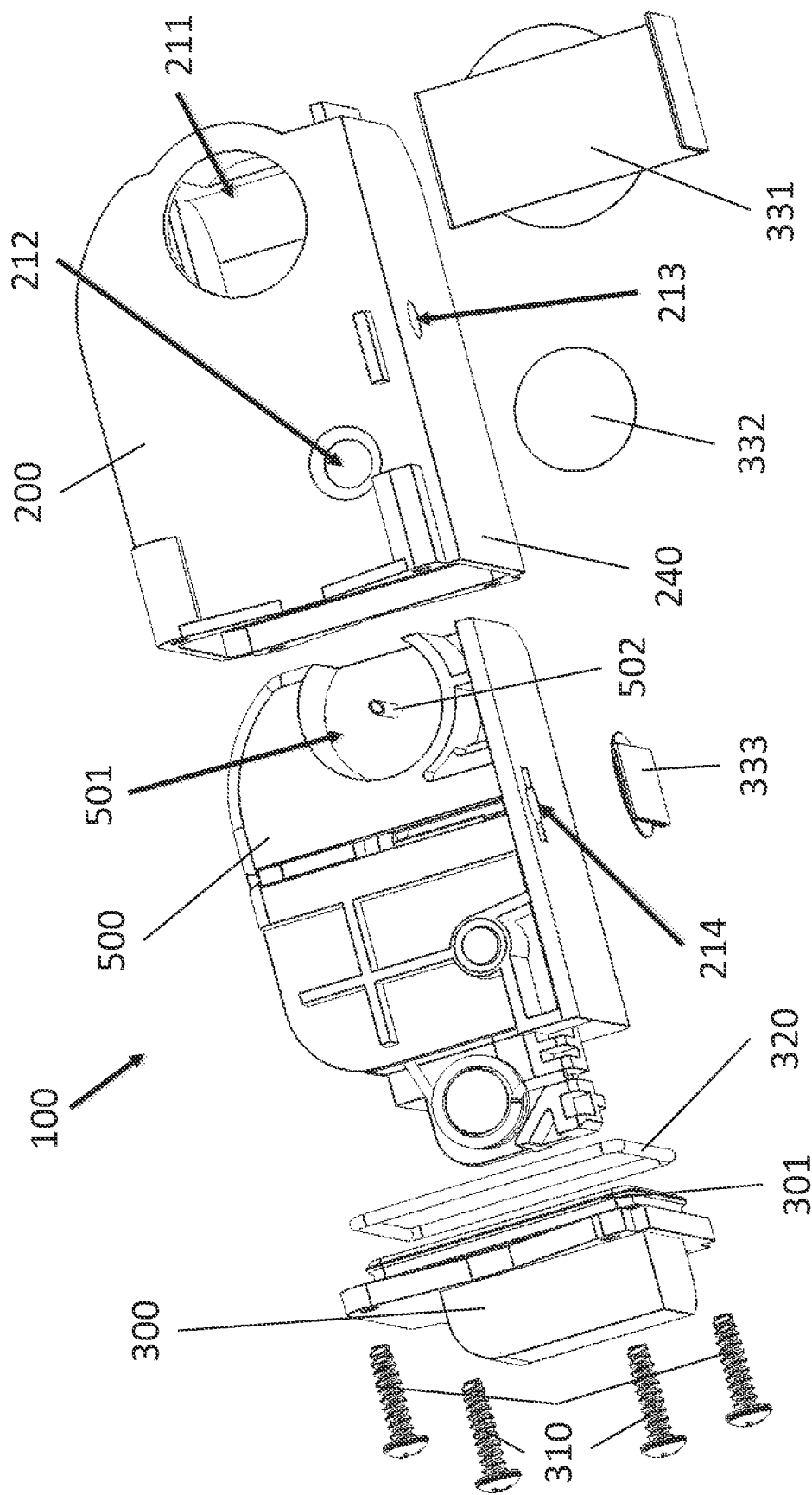
FIG. 1 shows an exploded view of an example needle insertor according to a first embodiment of the present disclosure.

FIG. 1 shows an exploded view of a needle insertor 100 according to the first embodiment of the present disclosure.

The needle insertor 100 includes a case 200, a cover 300, a plurality of fixing elements 310, an O-ring 320, a first seal 331, a second seal 332, and a third seal 333. The needle insertor 100 further includes an insertor assembly 500 positioned within the enclosure of the case 200 and cover 300. The structure of insertor assembly 500 will be further explained in details below.

The case 200 includes a first opening 211, a second opening 212, and a third opening 213 on an injection site end 240, wherein the injection site end 240 faces the injection site when a medicament delivery device having the needle insertor 100 is placed on the injection site. The first, second, and third seals 331, 332, 333 are configured to attach to the case 200 to cover the first, second, and third openings 211, 212, 213.

The insertor assembly 500 includes a container port 501 configured with a piercer 502 for piercing a medicament container. The insertor assembly 500 further includes a movable stop 530 (illustrated in FIG. 2) configured to be moved to activate the needle insertion sequence of the insertor assembly 500. The insertor assembly 500 includes a fourth opening 214 (illustrated in FIG. 1) corresponding to the third opening 213, wherein a needle within the insertor assembly 500 will pass through the third and fourth openings 213, 214 to penetrate the injection site. When the insertor assembly 500 is positioned inside the case 200, the piercer 502 and stop 530 will be respectively exposed through the first and second openings 211, 212 of the case 200. However, the first and second seals 331, 332 cover the two openings 211, 212 to ensure that external objects will not interact with the piercer 520 and stop 530 before the needle insertor 100 is ready for use. Similarly, the third seal 333 covers the third and fourth openings 213, 214 to ensure that no external objects interact with the needle within the insertor assembly 500 before the needle insertor 100 is ready for use.

The cover 300 is configured to couple with the case 200 and covers the opening through which the insertor assembly 500 is inserted into the case 200. The cover 300 includes an O-ring portion 301 surrounded by the O-ring 320. This arrangement allows the O-ring portion 301 and O-ring 320 to create a seal with the inner surface of case 200 when inserted into the case 200. In this embodiment, the fixing elements 310 are screws configured to pass through the corresponding screws openings on the case 200 and cover 300 to secure the two components 200, 300 together. Together, case 200, cover 300, and the first, second, third seals 331, 332, 333 ensure that external objects will not make contact with insertor assembly 500 before the needle insertor 100 is ready for use. Also, other suitable fixing elements known to a skilled person such as bolts can be used to secure the case 200 and cover 300 together.

FIG. 2 shows an exploded view of the insertor assembly 500 according to the first embodiment of the present disclosure. The insertor assembly 500 includes a base 510, a piercer 502, a cannula assembly 520, a movable stop 530, a driver 540, a needle assembly 550, a medicament path assembly 570, an energy accumulation member 580, a rotator 590, and a sleeve 600. The function of each component mentioned above and its relationship with the base 510 will be explained in more details below.

FIG. 3 shows an exploded view of the cannula assembly 520 and medicament path assembly 570. The cannula assembly 520 includes a cannula portion 521 and a cannula base portion 522. The cannula portion 521 and cannula base portion 522 are both hollow inside. The cannula base portion 522 has a hose opening 523 and a cannula mount 524 that has an opening to accommodate the cannula portion 521. The hollow cannula portion 521 is mounted on the cannula mount 524 to gain access to the inner space of the cannula base portion 522. Thus, once the cannula portion 521 is coupled with the cannula mount 524, liquid entering the hose opening 523 will be able to pass through the inner space of cannula base portion 522 and then exit through the cannula portion 521.

In the present embodiment, the medicament path assembly 570 includes an attachment pin 571, a first crimp 572, a second crimp 573, and a hose 574. The attachment pin 571 has a thicker portion configured to be fitted in the hose opening 523 to gain access to the inner space of cannula base portion 522. The attachment pin 571 also has a thinner portion configured to be coupled with one end of the hose 574, wherein the first crimp 572 surrounds the portion of hose 574 coupled with the attachment pin 571 to ensure that the two components are fastened. The second crimp 573 is configured to surround the portion of hose 574 coupled with the piercer 502 which will be explained with figure later.

In the present embodiment, the medicament path assembly 570 includes four components assembled together. In other embodiments, the medicament path assembly 570 can instead include only one tube or other number of components suitable to be assembled with the cannula assembly 520.

FIG. 4 shows an exploded view of the needle assembly 550 (see FIG. 4A), cannula assembly 520 (see FIG. 4B), and medicament path assembly 570 as well as a perspective view of the assembly of said components. The cannula assembly 520 and medicament path assembly 570 are assembled as described above. On the other hand, the needle assembly 550 includes a needle base portion 55 and needle portion 552 coupled together. The cannula base portion 522 includes a needle opening 525 for allowing access to the inner space of cannula base portion 522. Thus, the needle portion 552 can pass through the needle opening 525 and pass through the cannula portion 521 as illustrated on the right side of FIG. 4.

In the present embodiment, the cannula base portion 522 includes a base coupling key 526 having a protrusion 527. On the other hand, the needle base portion 551 has a coupling trough 553 configured to couple with the protrusion 527. Said structure ensures that the needle base portion 551 and cannula base portion 522 are coupled together in such as a way that external forces will not cause vibration of the needle base portion 551 that may cause damage to the needle portion 552 within the cannula portion 521. The configuration also serves to make sure that the cannula base portion 522 is coupled with a corresponding needle base portion 551. Also, in other embodiments, the protrusion 527 can be disposed on the needle base portion 551 while the corresponding coupling trough 553 is disposed on the base coupling key 526. Other suitable configuration can also be used to couple the needle base portion 551 with the cannula base portion 522.

FIG. 5 shows an exploded view of the energy accumulation member 580, rotator 590, and sleeve 600 as well as a perspective view of the assembly of said components. The rotator 590 has a driver end 591 and a coupling end 592 for passing through the energy accumulation member 580 and coupling with the sleeve 600. The drive end 591 is configured to interact with the driver 540 (illustrated in FIG. 2) when the rotator 590 is released to be rotated by the energy accumulation member 580. The sleeve 600 is hollow in order to accommodate both the energy accumulation member 580 and the rotator 590. The sleeve 600 has a rotator coupling opening 601 configured to allow the coupling end 592 to pass through and couple with the sleeve 600. Each of the two coupling ends 592 has a fin 593 extending and slanting radially outward. When the coupling end 592 is pressed against the inner surface of sleeve 600, the inner surface of sleeve 600 forces the slanting surface of fin 593 and coupling end 592 as a whole to flex radially inward. In this way, both the coupling ends 592 together become thin enough to pass through the rotator coupling opening 601. Afterward, the coupling ends 592 flex radially outward and the fins 593 engage the outer surface of sleeve 600 surrounding the opening 601 to prevent the rotator 590 from being pulled away. This coupling allows the rotator 590 to be rotatable relative to the sleeve 600 and prevents the rotator 590 to move longitudinally relative to the sleeve 600. On the other hand, the energy accumulation member 580 has two ends, one positioned between the two coupling ends 592 of rotator 590 and the other positioned in a notch 602 on the sleeve 600.

In the present embodiment, the energy accumulation member 580 is a torsion spring. However, in other embodiments, the energy accumulation member 580 can be other forms of force generating component capable of accumulating energy and release the energy when released.

Figure 6:
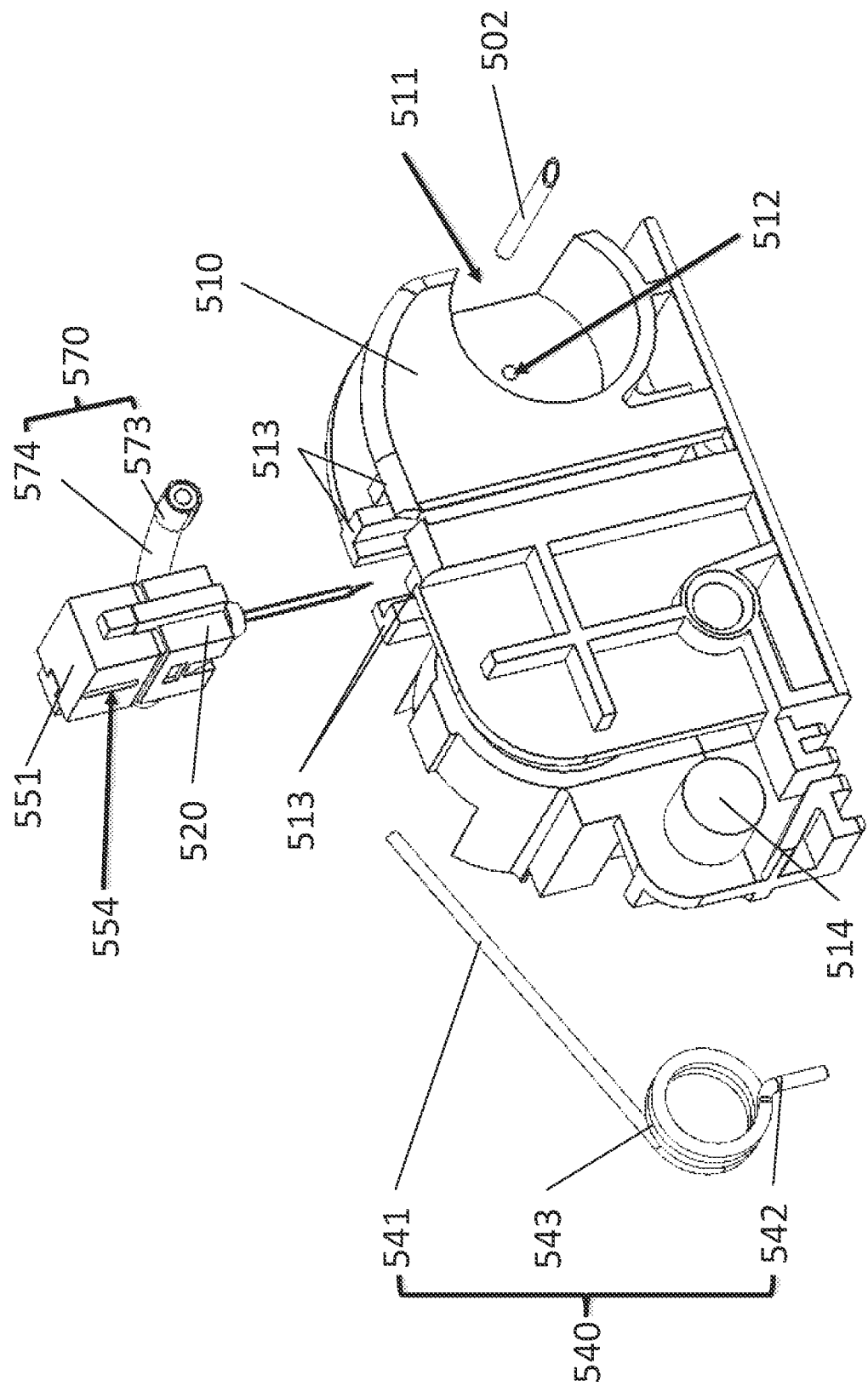
FIG. 6 shows an exploded view of the base, piercer, cannula assembly, driver, needle assembly, and medicament path assembly.
Figure 7:
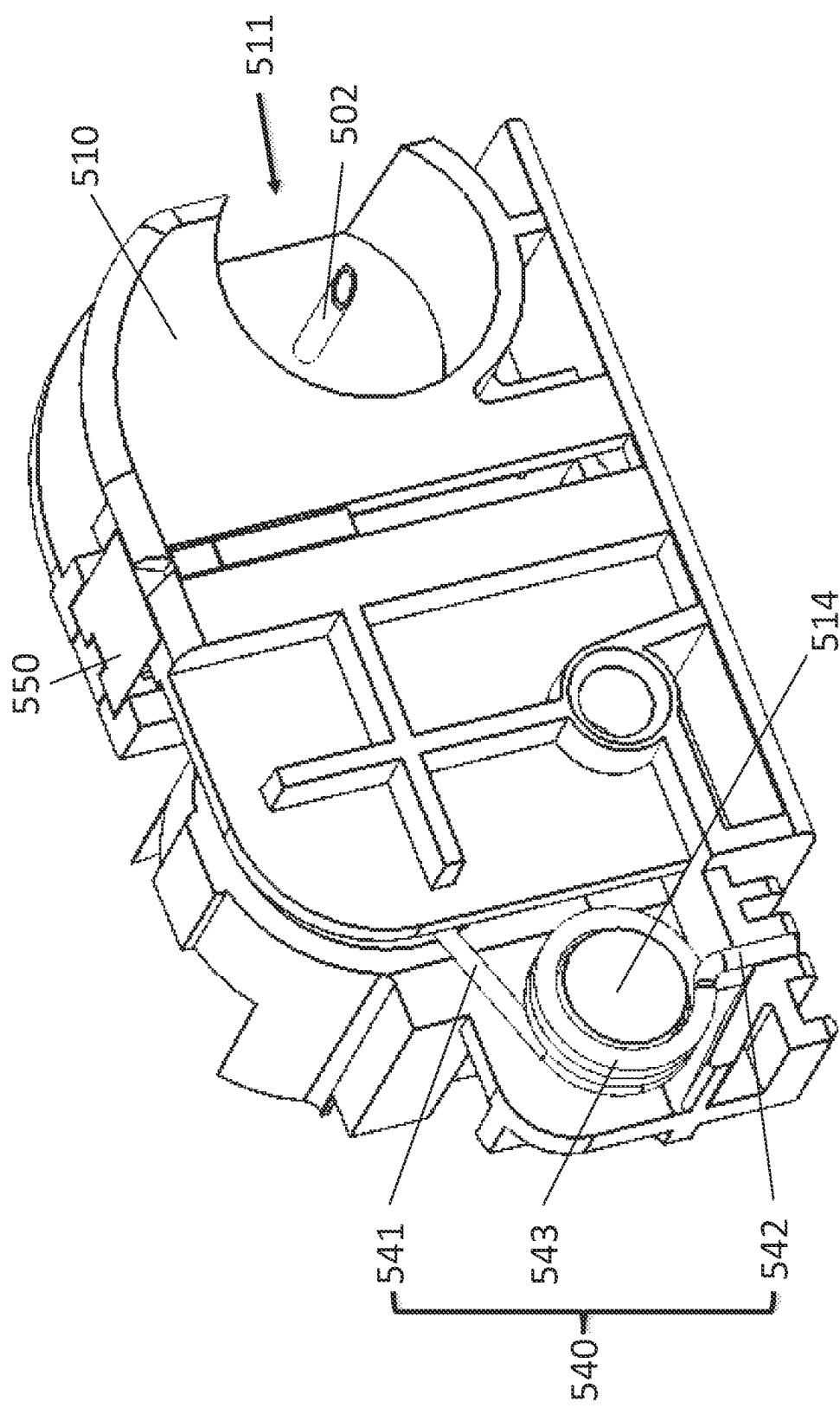
FIG. 7 shows a perspective view of the base, piercer, driver, needle assembly, cannula assembly, and medicament path assembly assembled.
Figure 8:
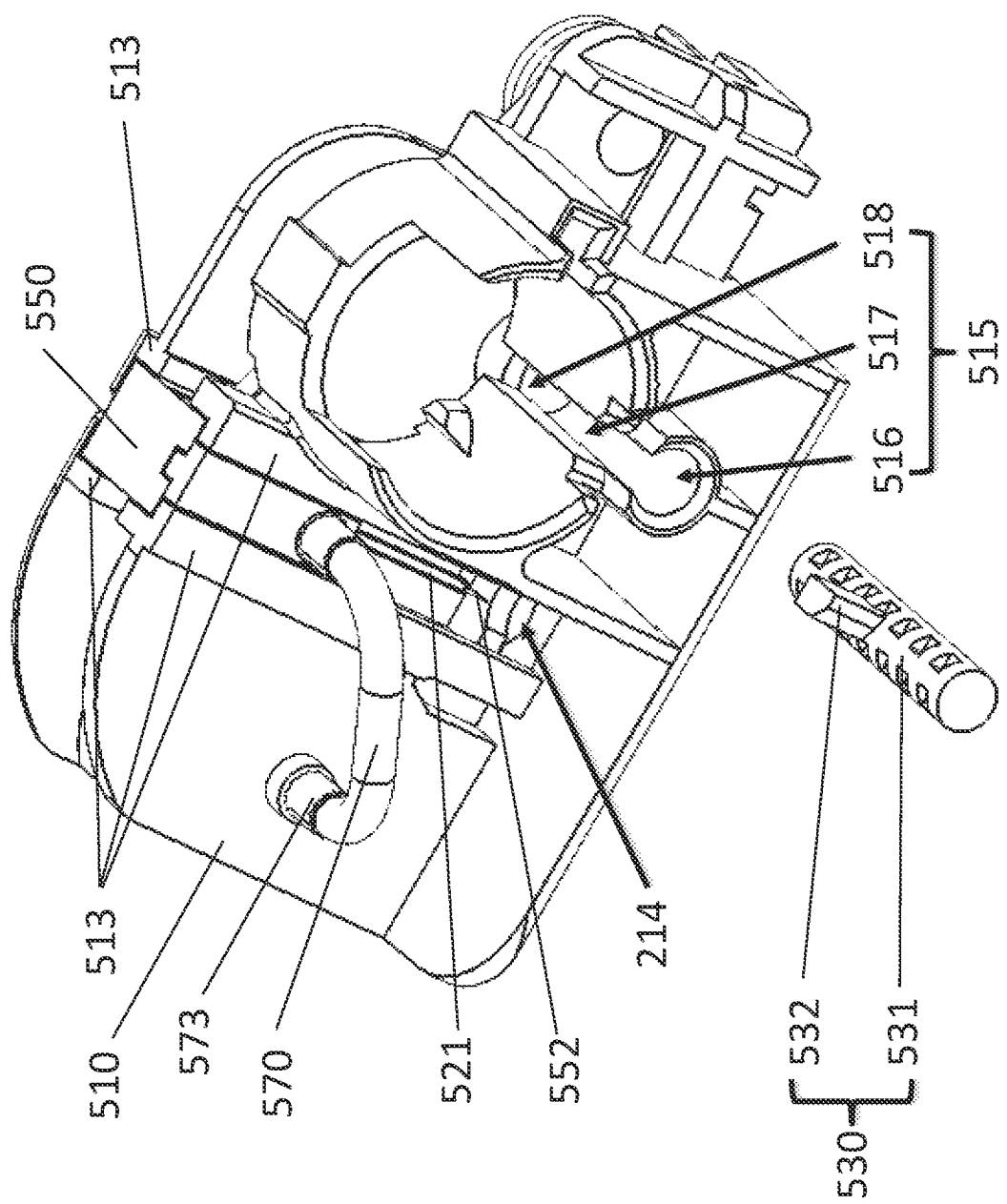
FIG. 8 shows a perspective view of a movable stop to be assembled with the base.

FIG. 6 shows an exploded view of the base 510, piercer 502, cannula assembly 520, driver 540, needle assembly 550, and medicament path assembly 570. FIGS. 7 and 8 show perspective views of the assembly of piercer 502, base 510, cannula assembly 520, driver 540, needle assembly 550, and medicament path assembly 570. The base 510 has a container port 511 for accommodating a medicament container and a piercer opening 512 for accommodating the piercer 502. In the present embodiment, the end of hose 574 surrounded by the second crimp 573 is positioned on one end of the piercer opening 512 while the piercer 512 passes through the other end of piercer opening 512 to be coupled with both the base 510 and hose 574. Thus, a medicament container can have its seal pierced to have the medicament within flowing through the piercer 502, hose 574, cannula base portion 522, and finally exit through the cannula portion 521.

In the present embodiment, the base 510 has a guiding structure 513 configured to accommodate and guide the insertion of the needle assembly 550 and cannula assembly 520. The guiding structure 513 creates a space with size and shape corresponding to those of the needle assembly 550 and cannula assembly 520. As illustrated in FIG. 8, the base 510 has the fourth opening 214 configured for the cannula portion 521 and needle portion 552 to pass through and reach the injection site.

As illustrated in FIGS. 6 and 7, the base 510 also has a driver rest 514 configured to couple with the driver 540. In the present embodiment, the driver 540 has a first part 541 configured to couple with the needle base portion 551, a second part 542, and a third part 543 configured to couple with the driver rest 514. As illustrated, the third part 543 of driver 540 has a circular opening with size corresponding to that of the driver rest 514. Thus, the base 510 and driver 540 can be coupled by putting the third part 543 on the driver rest 514 as illustrated in FIG. 7.

Further, as illustrated in FIG. 6, the needle base portion 551 has a driver opening 554 configured for the first part 541 of driver 540 to pass through to couple the driver 540 with the needle assembly 550. When the first part 541 is under no external forces it maintain the position of the needle assembly 550 on one end of guiding structure 513 away from the injection site opening 514, as illustrated in FIGS. 7 and 8. On the other hand, external forces may also be exerted on the first part 541 to move the needle assembly 550 toward the injection site opening 514 as will be explained later.

Here please refer to FIG. 8 for the explanation on installation of the movable stop 530. In the present embodiment, the base 510 has a stop rest 515 configured to accommodate the movable stop 530. The stop 530 has a main portion 531 and a first obstruction portion 532. On the other hand, the stop rest 515 is tubular and has a tunnel 516 for the main portion 531 to pass through and a gap 517 for the first obstruction portion 532 to pass through. One end of the tunnel 516 is disposed with stop openings 518 so that an external object can move the stop 530 by interacting with the main portion 531 through the stop openings 518.

Figure 9:
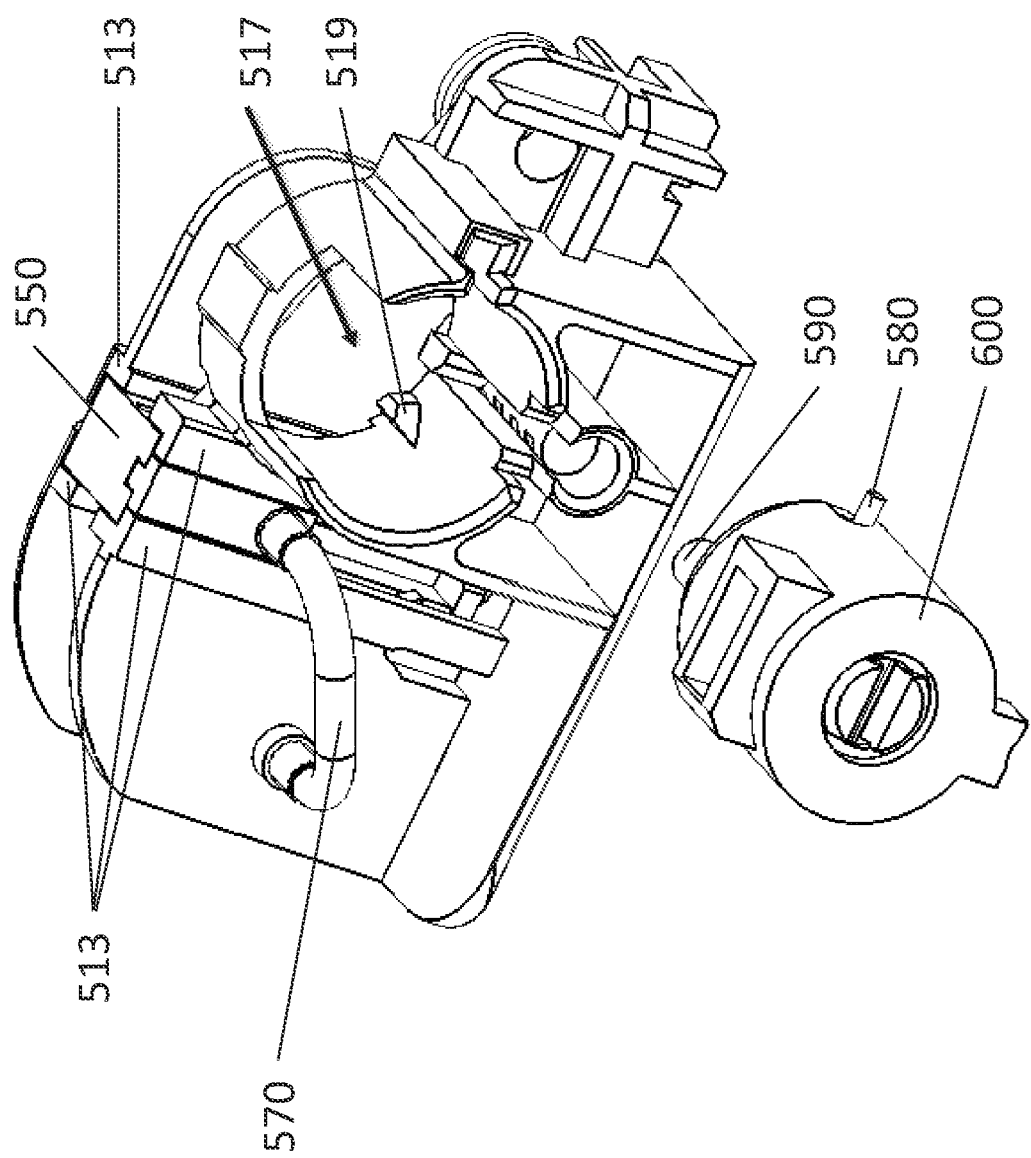
FIG. 9 shows a perspective view of a torsion spring, rotator, and sleeve to be assembled with the base.
Figure 10:
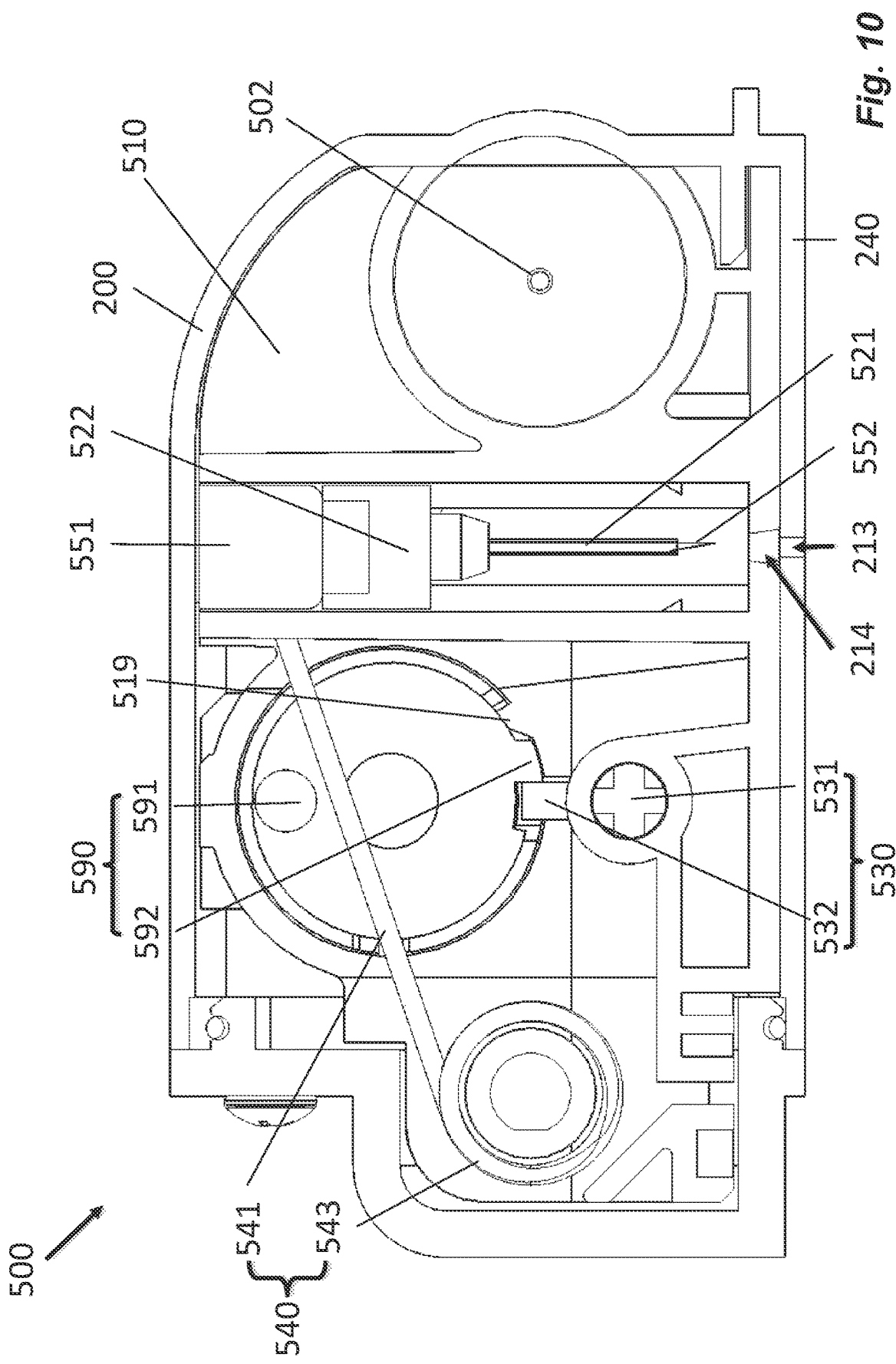
FIG. 10 shows a cross-section view of the needle insertor before the rotator is released.

Here please refer to both FIGS. 9 and 10 for the installation of the energy accumulation member 580, rotator 590, and sleeve 600 as well as the interaction between the stop 530 and rotator 590. In the present embodiment, the base 510 has a sleeve port 517 configured to accommodate the assembly of the energy accumulation member 580, rotator 590, and sleeve 600. The sleeve port 517 includes a second obstruction portion 519 disposed on the inner surface of the sleeve port 517. As illustrated in FIGS. 2 and 10, the rotator 590 includes a driving member 591 configured to interact with the first part 541 of driver 540 after the rotator 590 is released. Also as illustrated in FIG. 10, the rotator 590 also has an engagement member 592 configured to interact the first obstruction portion 532 of stop 530 before the rotator 590 is released. The engagement member 592 is also configured to interact with the second obstruction portion 519 after the rotator 590 is released. The interaction between components mentioned above will be explained in more details below.

When the assembly of the energy accumulation member 580, rotator 590, and sleeve 600 is inserted in the sleeve port 517 of base 510, the engagement member 592 of rotator 590 will be positioned between the gap/space between the obstruction portion 518 of sleeve port 517 and the first obstruction portion 532 of stop 530. See FIG. 10. In the present embodiment illustrated in FIG. 10, the energy accumulation member 580 constantly applies a rotational force on the rotator 590 in a clockwise direction. However, the first obstruction portion 532 prevents such clockwise rotation of the rotator 590 by engaging the engagement member 592. Unless the stop 530 is moved in order for the first obstruction portion 532 to disengage the engagement member 592, the energy accumulation member 580 will not be able to rotate the rotator 590 in a clockwise direction.

Figure 11:
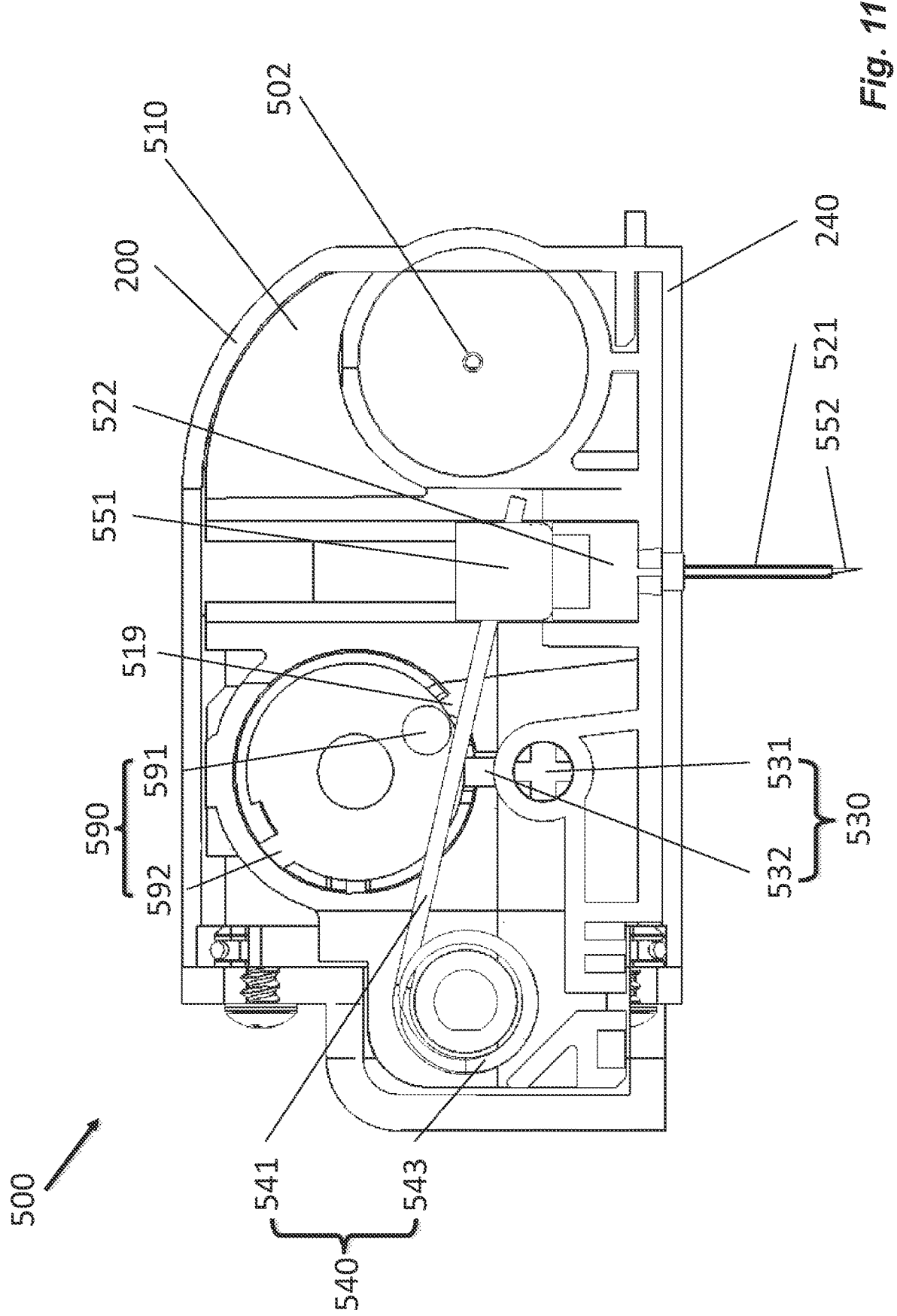
FIG. 11 shows a cross-section view of the needle insertor when the rotator is rotated by an associated torsion spring.

FIG. 11 shows a cross-section view of the needle insertor 100 after the stop 530 disengaged the rotator 590. An external object can be used to push the stop 530 exposed through the stop openings 518 of base 510. See FIG. 12. The result of the stop's 530 movement is that its first obstruction portion 532 is no longer in engagement with the engagement member 592 of rotator 590. Thus, the rotator 590 is promptly rotated under the rotational force of the energy accumulation member 580 in a clockwise direction. During such rotation, the driving member 591 interacts with the first part 541 of driver 540 and pushes the first part 541 downward toward the injection site end 240. As mentioned above, the first part 541 is coupled with the needle base portion 551 of needle assembly 550. Also, the needle base portion 551 is positioned above the cannula base portion 522 of cannula assembly 520. Thus, as the first part 541 is pushed downward, the first part 541 will also push both the cannula assembly 520 and needle assembly 550 downward. This downward movement results in both the needle portion 552 passing through the third opening 213 of case 200 and fourth opening 214 on the base 510 to pierce the injection site to create an opening. Similarly, the cannula portion 521 also passes through the injection site opening 514 and enters the injection site through the opening created by the needle portion 552. The needle penetration and cannula insertion procedures are complete.

Figure 12:
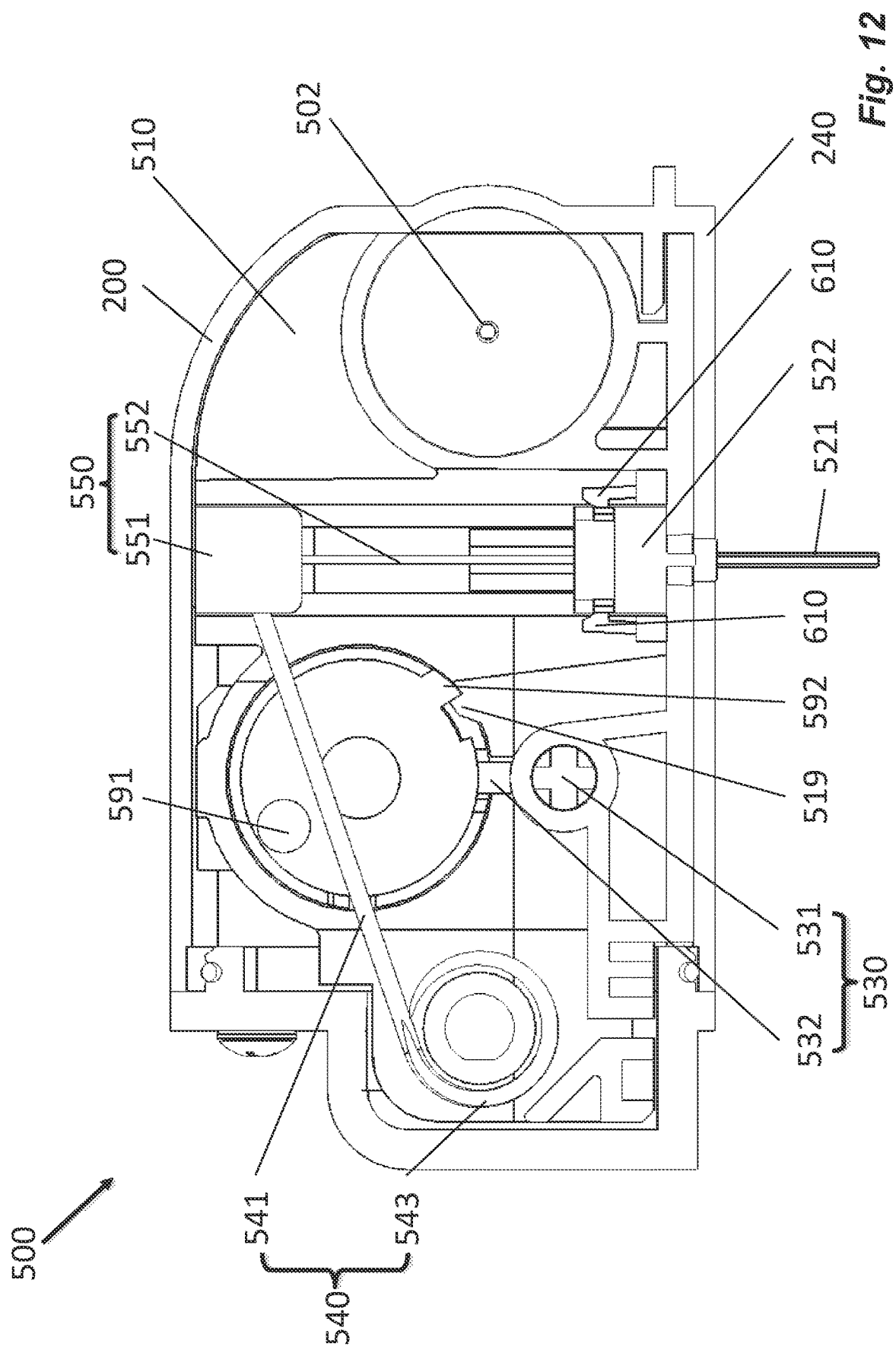
FIG. 12 shows a cross-section view of the needle insertor when the rotator retracts the needle portion back inside the case and is prevented from further rotating.

FIG. 12 shows a cross-section view of the needle insertor 100 after the rotator 590 is prevented from further rotating by the second obstruction portion 519 of sleeve port 517. As mentioned above, the energy accumulation member 580 constantly applies rotational forces on the rotator 590, even after the needle penetration and cannula insertion procedures have been accomplished. The rotator 590 eventually rotates to the point where its engagement member 592 engages the second obstruction member 519 and the energy accumulation member 580 can no longer rotate the rotator 590. See FIG. 12. At this moment, the driving member 591 is no longer in engagement with the first part 541. Thus, the resilient nature of the driver 540 allows the first part 541 to move upward. Since the first part 541 is coupled with the needle base portion 551, this movement also brings the needle assembly 550 as a whole upward.

On the other hand, the base 510 has a pair of locking members 610 disposed on its inner surface next to the injection site opening 514. In the present embodiment, the locking members 610 each have the shape of a hook. When the cannula assembly 520 is pushed toward the injection site opening 514, its cannula base portion 522 will push the locking members 610 radially outward in order to reach the inner surface of base 510. As the cannula base portion 522 reaches the inner surface of base 510, the locking members flex radially inward and then engage the cutout on the outer surface of cannula base portion 522. The hook shape of locking members 610 ensures that the cannula assembly 520 will not be brought back up together with the needle base portion 551 by the first part 541. Accordingly, the cannula assembly 520 and needle assembly 550 will separate when the first part 541 returns to its initial position. The needle retraction and cannula locking procedures are complete.

Now that the needle retraction and cannula locking procedures are complete, the needle portion 552 no longer occupies the space in the cannula portion 521. Thus, after a medicament container is inserted in the container port 501 to have its seal pierced by the piercer 502, the medicament within can flow through the piercer 502, hose 574, cannula base portion 522, cannula portion 521, and eventually enter the injection site.

Figure 13:
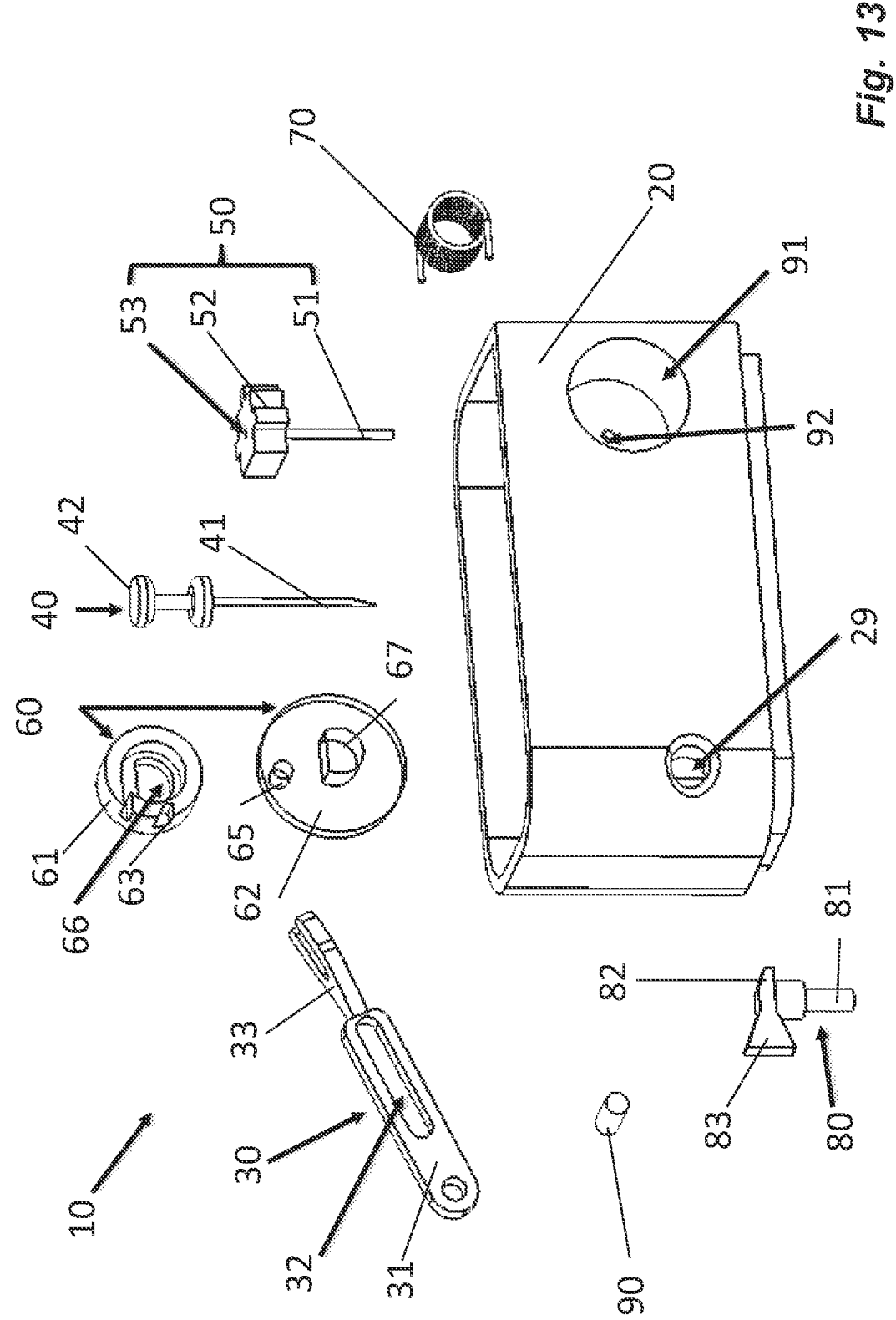
FIG. 13 shows an exploded view of an example needle insertor according to a second embodiment of the present disclosure.

FIG. 13 shows an exploded view of an example needle insertor 10 according to a second embodiment of the present disclosure. The needle insertor 10 includes a case 20, a driver arm 30, a needle assembly 40, a cannula assembly 50, a rotator 60, a torsion spring 70, a stop member 80, and a connection member 90, wherein the rotator 60 includes a first rotator 61 and a second rotator 62. The second rotator 62 is made transparent to facilitate illustration.

Figure 14:
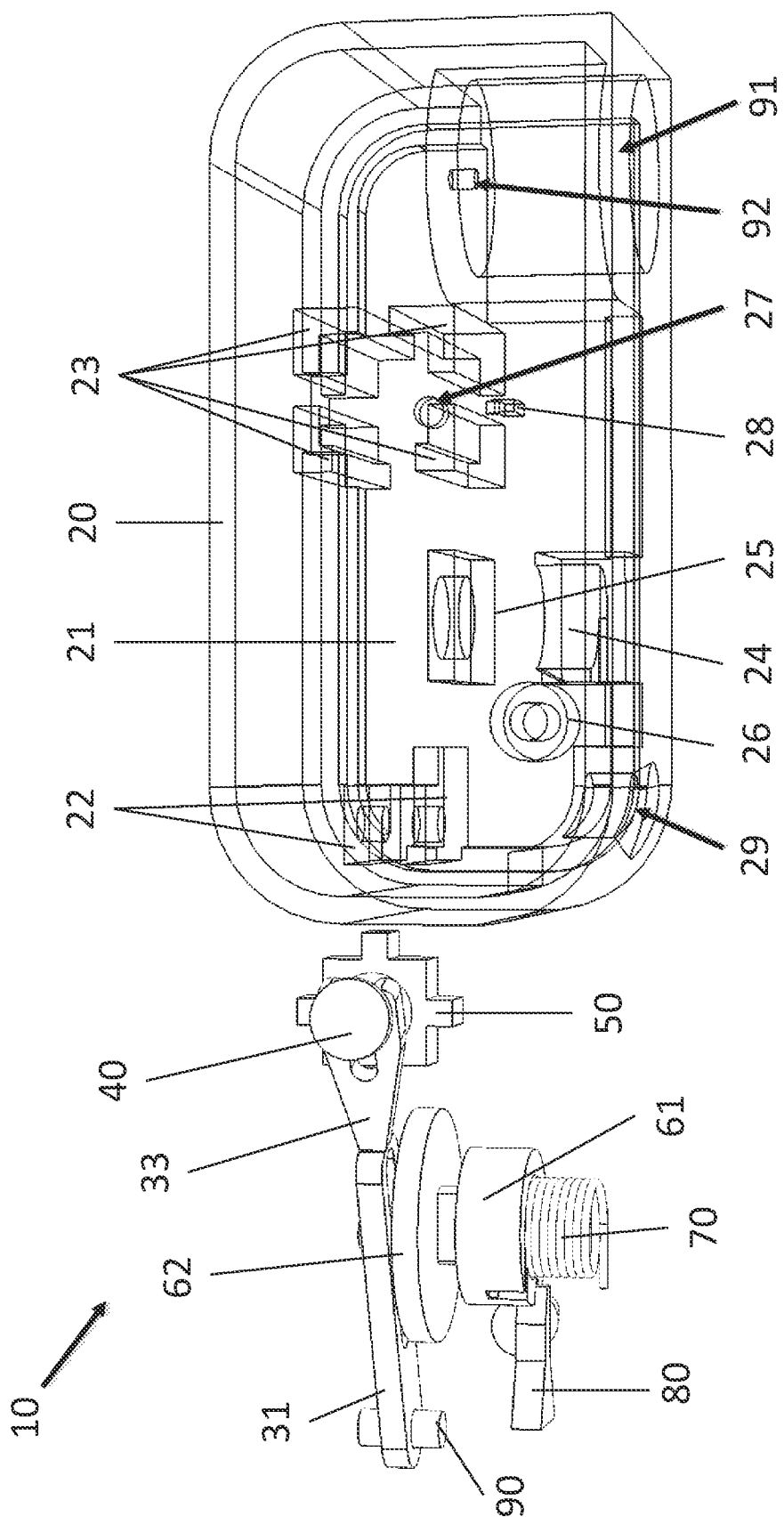
FIG. 14 shows a perspective view of the needle insertor according to a second embodiment of the present disclosure.

On the other hand, FIG. 14 shows a perspective view of the needle insertor 10 according to the second embodiment of the present disclosure. The case 20 is made transparent to facilitate the illustration. The case 20 includes a base 21 to accommodate the rest of the needle insertor 10, a driver arm portion 22 for coupling with one end of the driver arm 30, a guide structure 23 for accommodating the needle assembly 40 and the cannula assembly 50 and guiding the movement thereof, a first rotator stand 24 for accommodating the first rotator 61, a second rotator stand 25 for accommodating the second rotator 62, and a stop member stand 26 for accommodating the stop member 80. The base 21 includes a needle opening 27 for the needle assembly 40 and cannula assembly 50 to pass through and exits outside the case 20. The base 21 also includes a locking member 28 for later fixing the cannula assembly 50 on the base 21. The case 20 also includes an activation member opening 29 configured for an activation member (not illustrated) to pass through and interact with the stop member 80 and then release the rotator 60. The interaction between the elements on the case 20 with the rest of the needle insertor 10 will be further explained later.

In the present embodiment, the torsion spring 70 is accommodated in the space (illustrated in FIG. 13) carved out of the first rotator 61 and constantly exerts a rotational force on the first rotator 61. The first rotator 61 and torsion spring 70 are both placed on the first rotator stand 24.

As illustrated in FIG. 13, the stop member 80 has a first protrusion 81 configured to be inserted into the opening of the stop member stand 26 (illustrated in FIG. 14) in order to couple the stop member 80 with the base 21. However, the first protrusion 81 is not fixed within the stop member stand 26 and the stop member 80 is rotatable with respect to the axis of the stop member stand 26. The stop member 80 has a second protrusion 82 configured to couple with the first rotator 61 in order to prevent the rotator 60 as a whole from being rotated by the torsion spring 70. As illustrated in FIG. 13, the first rotator 61 includes a stop groove 63 configured to accommodate the second protrusion 82. As described above, the torsion spring 70 constantly applies rotational force on the first rotator 60. The second protrusion 82 can absorb the rotational force and prevent the first rotator 60 from rotating. The stop member 80 also has a third protrusion 83 configured to be pushed in order to rotate the second protrusion 82 in either a clockwise or anticlockwise direction. The purpose of the third protrusion 83 is to be rotated by user to subsequently rotate the second protrusion 82 out of the stop groove 63 in order to release the first rotator 61. As described above, the case 20 also includes an activation member opening 29 configured for an activation member (not illustrated) to pass through. The activation member can push the third protrusion 83 to rotate the second protrusion 82 out of the stop groove 63 so that the rotator 60 can be released and then rotated by the torsion spring 70.

The case 20 includes a container port 91 with a piercer opening 92 can be fitted with a piercer similar to the piercer 502 in the first embodiment. A medicament container can be inserted in the container port 91 to have its seal pierced so that the medicament within can flow through the piercer to reach the interior of case.

The first rotator 61 and second rotator 62 are meant to be coupled together so that the rotational force of the torsion spring 70 can rotate both rotators 61, 62 simultaneously. The first rotator 61 has a rotator opening 66 and the second rotator 62 has a corresponding rotator protrusion 67 configured to be fitted into the rotator opening 66. The shape of both the rotator opening 66 and rotator protrusion 67 are not circular so that the rotational force from the torsion spring 70 can be transferred from the first rotator 61 to the rotator protrusion 64 and then the second rotator 62 as a whole.

In the present embodiment, one first portion 31 of the driver arm 30 is rotatably coupled with the driver arm portion 22 of the case 20. The first portion 31 has an opening configured to be aligned with the two openings of the driver arm portion 22. The connection member 90 is then fitted in the space of the three openings in order to couple the driver arm 30 with the driver arm portion 22. Also, the connection member 90, opening of the first portion 31, and opening of the corresponding driver arm portion 22 preferably have circular shapes or other suitable shape in order for the first portion 31 to be rotatably coupled with the driver arm portion 22.

The driver arm 30 further includes a cam opening 32 and the second rotator 62 includes a cam 65 configured to be fitted within the cam opening 32. As described above, the rotational force from the torsion spring 70 rotates both the first rotator 61 and second rotator 62. The cam 65 fitted inside the opening 32 allows the second rotator 62 to directly interact with the driver arm 30. In this way, the rotational force can be transferred from the cam 65 to the driver arm 30. However, since the first portion 31 is coupled with the base 21 of the case 20, the rotational force from the cam 65 allows the cam 65 to travel within the cam opening 32 and will only pivot the driver arm 30 upward and downward. Thus, as long as the torsion spring 70 keeps the rotator 60 rotating, the driver arm 30 will continuously be pivoted upward and downward.

The introducer needle 40 includes a needle portion 41 and a needle base portion 42 located at one end of the needle portion 41. On the other hand, the driver arm 30 has a second portion 33 configured to grip the base portion 42. As the driver arm 30 is pivoted downward by the rotational force from the rotator 60, the second portion 33 will drive the base portion 42 as well as needle assembly 40 as a whole downward toward the base 20 so that the needle portion 41 can pass through the needle opening 27 on the base 21 to initiate needle penetration.

Figure 15:
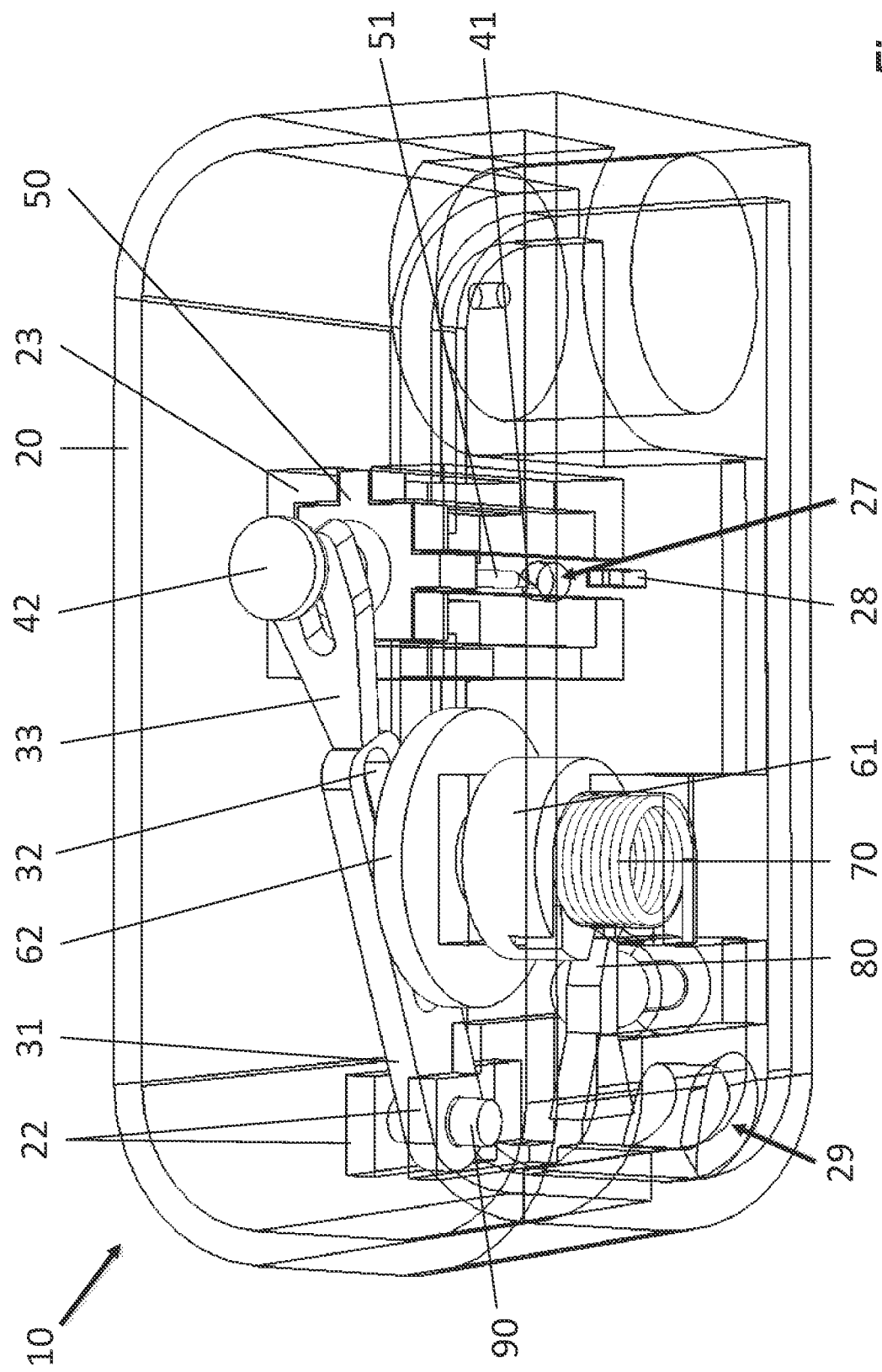
FIG. 15 shows another perspective view of the needle insertor according to a second embodiment of the present disclosure.

The cannula 50 includes a cannula portion 51 and a cannula base portion 52 located at one end of the cannula portion 51. The cannula base portion 52 has a first opening 53 that allows the needle portion 41 of the introducer needle 40 to pass through. The cannula portion 51 is hollow inside and the space inside the cannula portion 51 is connected to the first opening 53 of the cannula base portion 52. Also, the needle portion 41 is longer than the cannula portion 51. Thus, the needle portion 41 of the needle assembly 40 can go all the way through the cannula portion 51 so that its sharp end can emerge outside the cannula portion 51. See FIG. 15. As the needle portion 41 pass through the cannula portion 51, the base portion 42 of the needle assembly 40 will abut the cannula base portion 52 of the cannula 50. Afterwards, the force moving the needle assembly 40 will be transferred to the cannula assembly 50 and move the needle assembly 40 and cannula assembly 50 together downward toward the base 21. Also, as illustrated in FIG. 14, the guide structure 23 is configured to accommodate the shape of the base portion 52 of the cannula 50. The guide structure 23 has gaps corresponding to the three protrusions on the cannula base portion 52. Thus, each of the protrusions is only allowed to move with the corresponding gap. The shape of the central passage of the guide structure 23 also corresponds in shape to that of the cannula base portion 52. The reason for the guide structure 23 to have shapes corresponding to those of the base portion 52 is to ensure that the needle assembly 40 and cannula assembly 50 remain at least substantially perpendicular to the base 21 at all times. Also, the cannula base portion 52 includes a second opening (not illustrated) configured to be connected with a medicament tube for medicament to pass through. The second opening is connected to the cannula portion 51. Thus, the medicament passing through the second opening can enter the cannula base portion 52, the cannula portion 51, and eventually the injector site.

As mentioned above, the container port 91 with a piercer allows a medicament container to be inserted to have its seal pierced so that the medicament within can flow through the piercer to reach the inside of case. A tube can be used to connect with the piercer and the second opening of cannula base portion 52. In this way, medicament within the container can flow through the piercer, tube, cannula base portion 52, and cannula portion 51 to eventually enter the injection site.

Initially, the second protrusion 82 of the stop member 80 is located in the stop groove 63 of the first rotator 61 to absorbs the torsion spring's forces and prevent the rotator 60 from rotating. Until the second protrusion 82 moves out of the stop groove 63, nothing will happen.

Then, an activation member passes through the activation opening 29 of the case 20 to push the third protrusion 83 and rotate the second protrusion 82 out of the stop groove 63. The moment the second protrusion 82 leaves the stop groove 63, the forces of the torsion spring 70 will force the first rotator 61 and the second rotator 62 to start rotating. As the second rotator 62 rotates, cam 65 of the second rotator 62 located inside the cam opening 32 will transfer the forces to the driver arm 30 to press the driver arm 30 downward toward the base 21. Also, since the first portion 31 of the driver arm 30 is fixed on the driver arm portion 22 of the case 20, the driver arm 30 as a whole will be pivoted relative to the driver arm portion 22. The forces on the second portion 33 are transferred to base portion 42 of the needle assembly 40 and subsequently the cannula base portion 52 of the cannula assembly 50. The forces moves both the needle assembly 40 and cannula 50 downward toward the base 21 and the two components are maintained perpendicular to the base 20 due the guidance of the guide structure 23 surrounding the two components.

The needle portion 41 of the needle assembly 40 will pass through the needle opening 27 on the base 21 to create an opening by piercing an injector site which is typically the user's skin. The cannula portion 51 then follows the needle portion 41 and enters the injection site. Further, when the cannula base portion 52 of the cannula 50 reaches its lower position, it will substantially make contact with the base 21. The locking member 28 on the base 21 will couple with the cannula base portion 52 to fix the cannula base portion 52 on the base 21 and the cannula portion 51 at least partly within the injector site.

The locking member 28 of the present embodiment is similar to the locking member 610 in the previous embodiment and has the shape of a hook. When the cannula assembly 50 is pushed toward the base 21, its cannula base portion 52 will push the locking members 28 outward in order to reach the base 21. As the cannula base portion 52 reaches the base 21, the locking members 28 returns to their initial positions and respectively engages the cannula base portion 52. The hook shape of locking members 28 ensures that the cannula assembly 50 will not be brought back up later with the needle assembly 40 by the driver arm 30. In other words, the cannula assembly 50 and needle assembly 40 will separate when driver arm 30 returns to its initial position.

After the needle portion 41 passes through the needle opening 27 on the base 21, the torsion spring 70 continues to rotate the rotator 60 and the cam 65 of the second rotator 62 can continue to pivot the driver arm 30. Afterward, the forces from the torsion spring 70 will force the cam 65 within the cam opening 32 to pivot the driver arm 30 upward and away from the base 21. Since the second portion 33 of the driver arm 30 is coupled with the base portion 42 of the needle assembly 40, the driver arm 30 will retract the needle assembly 40 back into the case 20.

During this movement, the needle portion 41 is pulled out of the injection site and passes through the space within the cannula 50 to create a clear passage from the second opening of the base portion 52 to the opening of the cannula portion 51. In this way, the medicament can then flow through the second opening 55 and exit the cannula portion 51 in order to enter the injection site for medicament injection. At this stage, the needle insertor 10 has accomplished its purpose of creating an opening on the injection site using the needle assembly 40, inserting the cannula 50 into the injection site, and retracting the needle assembly 40 back into the case 20 in order to create a passage for medicament to flow through the cannula 50 and enter the injection site.

In the Figures, various engagement features for are shown for providing an engagement between one or more components of the drug delivery device. The engagement features may be any suitable connecting mechanism such as a snap lock, a snap fit, form fit, a bayonet, lure lock, threads or combination of these designs. Other designs are possible as well.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. A needle insertor for a medicament delivery device, comprising:
   a case having a base and an injection site end, where the base comprises a circular driver rest;
   a driver having a first part movably arranged within the case and having a terminal end, a second part connected to the base and a third part circumferentially coupled to an outside surface of the driver rest;
   a needle assembly comprising an opening and movably held by the first part of the driver in the case, where the terminal end of the first part is positioned within the opening, and where the needle assembly includes a needle portion positioned substantially perpendicular to the injection site end;
   a rotator having an axis of rotation arranged in the case and configured to interact with the first part of the driver for moving the driver;
   an energy accumulation member configured to interact with the rotator for applying a rotational force on the rotator; and
   a movable stop slidably arranged within a sleeve port on the base and comprising an obstruction member that engages with the rotator to prevent the rotator from rotating;
   wherein the terminal end of the first part during engagement with the opening rotates about the driver rest from a first position where the needle assembly is held inside the case, to a second position where the needle portion is positioned outside the case after being moved to pass through the injection site end and pierce an injection site, and to a third position where the needle portion is positioned inside the case, and
   wherein a sliding movement of the movable stop relative to the base and along an axial path that is parallel to the axis of rotation disengages the obstruction member from the rotator to allow the rotational force from the energy accumulation member to rotate the rotator along the axis of rotation to further allow the first part to move between said positions.

2. The needle insertor of claim 1, further comprising a cannula assembly configured to interact with the needle assembly, wherein the cannula assembly remains within the case when the first part is in the first position, the cannula assembly is moved by the needle assembly to enter the injection site when the first part is in the second position.

3. The needle insertor of claim 2, wherein the cannula assembly includes:
   a cannula base portion; and
   a cannula portion substantially perpendicular to the injection site end, coupled with the cannula base portion, and configured to enter the injection site when the first part is in the first position, wherein the cannula portion is positioned in the injection site when the first part is in the second position.

4. The needle insertor of claim 3, wherein the cannula base portion includes a medicament input opening, the cannula portion and cannula base portion are hollow so that a medicament can pass through the medicament input opening, the cannula base portion, and exits through the cannula portion.

5. The needle insertor of claim 3, wherein the needle portion is positioned within the cannula portion when the first part is in the first and second positions, the needle portion is not positioned within the cannula portion when the first part is in the third position.

6. The needle insertor of claim 3, wherein the cannula base portion is positioned between the needle assembly and the injection site end, the needle assembly interacts with the cannula base portion to move the cannula assembly toward the injection site end when the first part moves from the first position to the second position.

7. The needle insertor of claim 2, wherein the base includes at least one locking member configured to engage and fix the cannula assembly on the base when the first part reaches the second position.

8. The needle insertor of claim 2, wherein the base includes:
   a container port for accommodating a medicament container;
   a piercer coupled with the container port for piercing the medicament container;
   a medicament path assembly coupled with the base, the medicament path assembly having a first end connected to the piercer and a second end connected to the cannula assembly;
   wherein a medicament can flow from the medicament container through the piercer and the medicament tube assembly to enter the cannula assembly.

9. The needle insertor of claim 1, wherein the needle assembly includes:
   a needle base portion coupled with the needle portion and configured to be movably held by the first part, wherein the first part drives the needle base portion to move the needle portion outside the case when moving from the first position to the second position, the first part drives the needle base portion to move the needle portion back inside the case when moving from the second position to the third position.

10. The needle insertor of claim 1, wherein the rotator includes an engagement member configured to interact with the first part, the engagement member of the rotator rotated by the energy accumulation member interacts with the first part to move the first part between said positions.

11. The needle insertor of claim 10, wherein the driver has a flexible elastic structure, the second part of the driver moves the first part of the driver to the third position when the engagement member no longer interacts with the first part.

12. The needle insertor of claim 1, wherein the base includes:
   a first rest configured to accommodate the energy accumulation member; and
   a second rest configured to engage the rotator and keep the rotator rotatably connected to the base.

13. The needle insertor of claim 1, wherein the injection site end of the case includes a first injection site opening configured for the needle assembly to pass through and pierce the injection site.

14. The needle insertor of claim 13, wherein the base includes a second injection site opening corresponding to the first injection site opening, the needle assembly passes through both the first and second injection site openings to pierce the injection site.

15. A medicament delivery device comprising:
   the needle insertor as claimed in claim 1; and
   a container port comprising a piercer positioned perpendicular to the needle portion.

16. A needle insertor for a medicament delivery device, comprising:
   a case having a base and an injection site end, where the base comprises a circular driver rest;
   a driver having a first part movably arranged within the case and having a terminal end, a second part connected to the base and a third part circumferentially coupled to an outside surface of the driver rest;
   a needle assembly comprising an opening and movably held by the first part of the driver in the case, where the terminal end of the first part is positioned within the opening, and where the needle assembly includes a needle portion positioned substantially perpendicular to the injection site end;
   a container port configured to hold a medicament container, where the container port is positioned on the base such that a longitudinal axis of the medicament container is generally perpendicular to the needle portion;
   a rotator having an axis of rotation arranged in the case and configured to interact with the first part of the driver for moving the driver;
   an energy accumulation member configured to interact with the rotator for applying a rotational force on the rotator; and
   a movable stop slidably arranged within a sleeve port on the base and comprising a first obstruction member that engages with the rotator for preventing the rotator from rotating;
   wherein the terminal end of the first part during engagement with the opening rotates about the driver rest from a first position where the needle assembly is held inside the case, to a second position where the needle portion is positioned outside the case after being moved to pass through the injection site end and pierce an injection site, and to a third position where the needle portion is positioned inside the case, wherein a sliding movement of the movable stop along an axial path that is parallel to the axis of rotation disengages the first obstruction member from the rotator to allow the rotational force from the energy accumulation member to rotate the rotator to further allow the first part to move between said positions, and
   wherein the rotation of the rotator stops when the rotator engages a second obstruction member.

17. The needle insertor of claim 16, where in the container port further comprises a piercer positioned generally perpendicular to the needle portion.

18. The needle insertor of claim 16, further comprising a cannula assembly configured to interact with the needle assembly, wherein the cannula assembly remains within the case when the first part is in the first position, the cannula assembly is moved by the needle assembly to enter the injection site when the first part is in the second position.

19. The needle insertor of claim 16, further comprising a cannula base portion that includes a medicament input opening, where the cannula portion and cannula base portion are hollow so that a medicament can pass through the medicament input opening, the cannula base portion, and exits through the cannula portion.

* * * * *